United States Patent [19]

Weber

[11] 4,118,560

[45] Oct. 3, 1978

[54] SUBSTITUTED 1,4-BIS-STYRYLBENZENE AND 4,4'-BIS STYRYLBIPHENYL AND THEIR USE AS OPTICAL BRIGHTNERS

[75] Inventor: Kurt Weber, Basel, Switzerland

[73] Assignee: Ciba-Geigy Corporation, Ardsley, N.Y.

[21] Appl. No.: 740,706

[22] Filed: Nov. 11, 1976

[30] Foreign Application Priority Data

Nov. 24, 1975 [CH] Switzerland .................. 15198/75

[51] Int. Cl.² ........................................... C07D 319/08
[52] U.S. Cl. .................................... 542/447; 542/459; 542/466; 252/79.1; 252/89 B; 252/89 R; 427/158
[58] Field of Search .................. 260/240 D, 340.3; 542/447, 459, 466; 252/79.1, 89; 427/158

[56] References Cited

U.S. PATENT DOCUMENTS

| 2,391,137 | 12/1945 | Danuser et al. | 260/340.3 X |
| 3,177,153 | 4/1965 | Pommer et al. | 542/453 X |
| 3,984,399 | 10/1976 | Weber et al. | 260/240 D X |
| 3,991,049 | 11/1976 | Siegrist et al. | 260/240 D |

OTHER PUBLICATIONS

Voltz, S. "Dyeing of Polyacrylonitrile Fibers with Azatrimethine Cyanines", in Angew Chem. Internat., vol. 1, 1962, No. 10, pp. 532–537.

*Primary Examiner*—Winston A. Douglas
*Assistant Examiner*—Thomas A. Waltz
*Attorney, Agent, or Firm*—Edward McC. Roberts; Prabodh I. Almaula

[57] ABSTRACT

Novel 1,4-bis-styryl-phenyl and 4,4'-bis-styryl-biphenyl derivatives, a process for their preparation, a process for optically brightening organic materials on using said compounds as well as detergent compositions containing said compounds are disclosed.

10 Claims, No Drawings

SUBSTITUTED 1,4-BIS-STYRYLBENZENE AND 4,4'-BIS STYRYLBIPHENYL AND THEIR USE AS OPTICAL BRIGHTNERS

The present invention provides novel styryl compounds, a process for their manufacture, and a method of using these compounds as fluorescent whitening agents for organic materials.

Distyryl-benzene and distyryl-diphenyl derivatives whose terminal phenyl radicals are mono- or polysubstituted are already known from the literature, for example from U.S. Pat. Nos. 3,849,485 and 3,907,904.

It has now been found that distyryl-benzene and distyryl-diphenyl derivatives which contain a 1,3-dioxane ring fused to at least one terminal phenyl radical possess more advantageous properties.

The distyryl compounds of the present invention have the formula

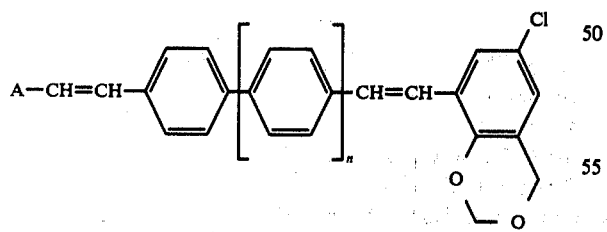

wherein A represents a radical of the formula

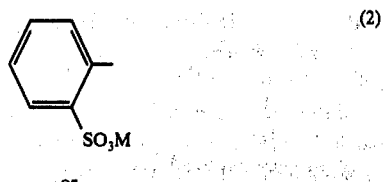

or

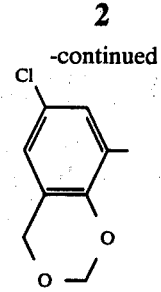

and $n$ is 0 or 1, whilst M represents a hydrogen atom or a salt-forming cation.

A suitable salt-forming cation is preferably an alkali metal, alkaline earth metal, ammonium or amine ion.

Within the scope of the above definition, particularly preferred compounds are those of the formulae

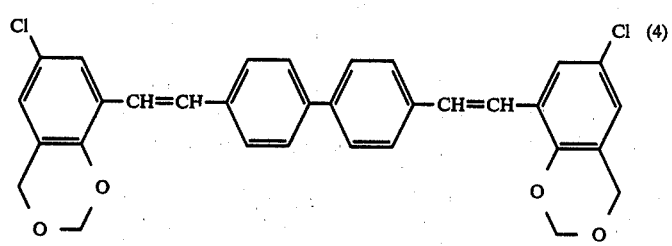

and

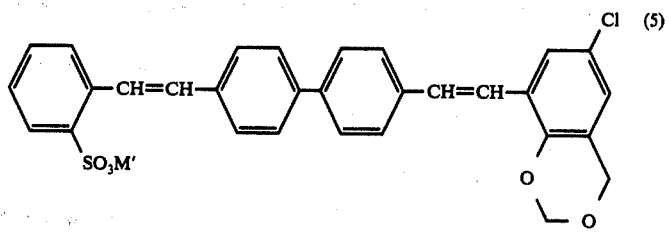

wherein M' represents an alkali metal, alkaline earth metal, ammonium or amine ion.

The distyryl compounds of the formula (1) can be obtained by methods which are known per se, for example be reacting 1 molar equivalent of a compound of the formula

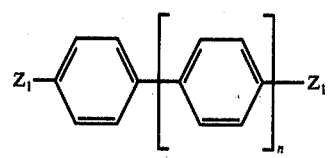

wherein $n$ is as defined in formula (1), with 1 molar equivalent of a compound of the formula

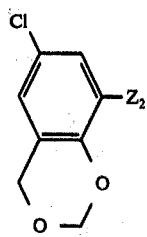

and 1 molar equivalent of a compound of the formula $$A-Z_2 \qquad (8)$$

wherein A is as defined in formula (1), whilst one of the symbols $Z_1$ and $Z_2$ represents an OHC group and the other represents one of the groups of the formulae

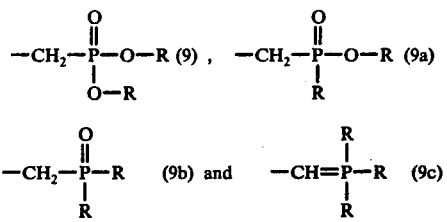

wherein R represents an unsubstituted or substituted alkyl group, preferably of 1 to 6 carbon atoms, an aryl group, preferably a phenyl group, a cycloalkyl group, preferably a cyclohexyl group, or an aralkyl group, preferably a benzyl group.

Compounds of the formula (4) are thus obtained by reacting 1 molar equivalent of the compound of the formula (6), wherein n is 1, with 2 molar equivalents of the compound of formula (7), and compounds of the formula (5) are obtained by reacting 1 molar equivalent of the compound of formula (6), wherein n is 1, with 1 molar equivalent of each of the compounds of formulae (2) and (3).

It is thus possible to react for example dialdehydes of formula

 (10)

with monofunctional compounds of the formulae

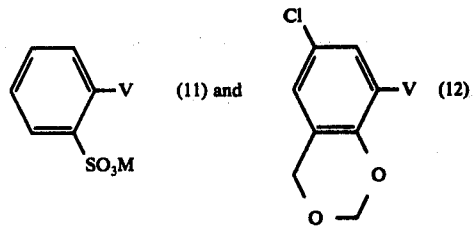

or monoaldehydes of the formulae

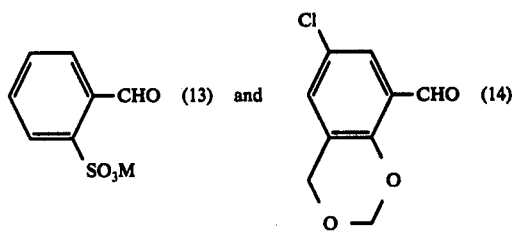

with bifunctional compounds of the formula

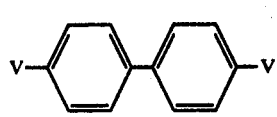 (15)

wherein M has the indicated meaning and V represents one of the groups of the formulae (9) to (9c).

The phosphorus compounds of the formulae (11), (12) and (15) used as starting materials are obtained in a manner known per se, by reacting halogenomethyl compounds, preferably chloromethyl or bromomethyl compounds, of the formulae

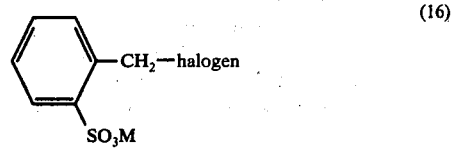

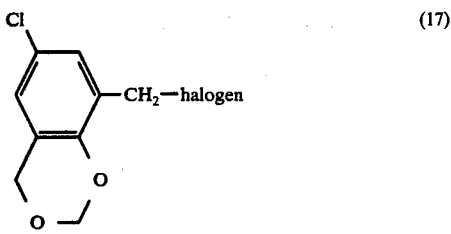

or

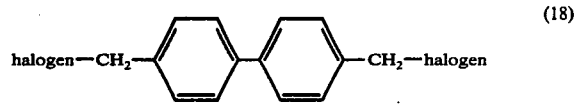

wherein M has the indicated meaning and halogen preferably represents a chlorine or bromine atom, with phosphorus compounds of the formulae

 (19)

 (20)

 (21)

or

 (22)

In these formulae, R has the indicated meaning, whilst groups R bonded to oxygen are preferably lower alkyl groups, and groups R directly bonded to phosphorus are preferably aryl groups, such as benzene residues. The phosphorus compounds of the formulae (11), (12) or (15) can also be obtained by reacting halogenomethyl compounds, preferably chloromethyl or bromomethyl compounds, of the formulae (16), (17) or (18), with p-chlorodiphenylphosphine, and subsequent reaction with an alcohol of the formula R—OH (wherein R is as previously defined herein), for example with methanol or with water.

Of the process modifications indicated above, the one particularly suitable for obtaining compounds of the formula (4) and (5) is that wherein 1 molar equivalent of a compound of the formula

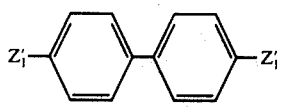
(23)

is reacted with 1 molar equivalent of each of the compounds of the formulae

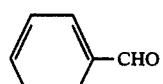
(13)

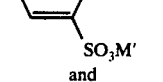

and

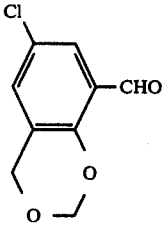
(14)

wherein M' has the indicated meaning and $Z_1$ represents a group of the formulae

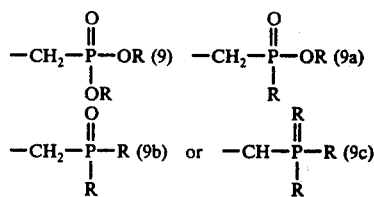

wherein R represents an unsubstituted or substituted alkyl, cycloalkyl, aryl or aralkyl group.

A particularly preferred modification of the process consists in using as diphenyl components of formula (15) those having the formula

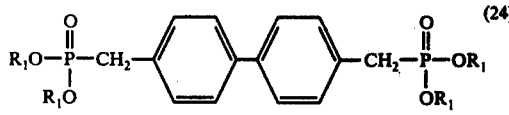
(24)

wherein $R_1$ represents an alkyl group of 1 to 6 carbon atoms.

The manufacturing process is advantageously carried out in inert solvents. Examples of inert solvents are: hydrocarbons such as toluene and xylene, or alcohols, such as methanol, ethanol, isopropanol, butanol, glycols, glycol esters, such as 2-methoxyethanol, hexanols, cyclohexanol and cyclooctanol, also ethers, such as diisopropyl ether, tetrahydrofurane and dioxan, as well as dimethyl sulphoxide, formamide, and N-methylpyrrolidone. Polar organic solvents are particularly suitable, for example dimethyl formamide and dimethyl sulphoxide. It is also possible to carry out a number of the reactions in aqueous solution.

The temperature at which the reaction is carried out can vary within wide limits. It is determined by (α) the resistance of the solvent employed to the reactants, especially to the strongly basic alkali compounds, (β) the reactivity of the condensation partners, and (γ) the strength of the combination of solvent and base as condensation agent.

In practice, temperatures between about 10° C. and 100° C. are normally possible, especially if either dimethyl formamide or dimethyl sulphoxide is used as solvent. The preferred temperature range is between 20° C. and 60° C. However it is also possible to apply higher temperatures if this is desired in order to save time or if a less active but cheaper condensation agent is to be used. In principle, therefore, reaction temperatures between 10° C. and 180° C. are also possible.

Suitable strongly basic alkali compounds are chiefly the hydroxides, amides and alcoholates (preferably those of primary alcohols containing 1 to 4 carbon atoms) of alkali metals: for reasons of economy, those of lithium, sodium and potassium are preferred. However, in principle and in special cases it is also possible to use with success alkali sulphides and alkali carbonates, arylalkali compounds, for example phenyl-lithium or strongly basic amines (including ammonium bases, for example trialkylammonium hydroxides).

In accordance with the above described process, chiefly mixtures of asymmetrically substituted distyryl compounds and the two corresponding symmetrically substituted distyryl compounds are obtained in the manufacture of distyryl compounds of the formula (1), wherein A is the radical of the formula (2), and especially of the formula (5), because of competition reactions of the three reactants. The separation of these components can be effected on account of their different solubility in water by isolating the water-insoluble compound by filtration. The water-soluble compounds remaining in the filtrate can then be separated on the basis of their varying degree of solubility in water.

Within the scope of the present invention, it is also possible — depending on the particular technical aspects of their use — to use the compounds of the formula (1) described herein, in which A is the radical of the formula (2), in admixture with the symmetrical corresponding compounds obtained from the competition reaction, for optical brightening. This fact means that, in actual practice and depending on the intended use, separation of the competing reaction products can also be dispensed with. If appropriate, the symmetrical water-insoluble compound can be isolated, whilst the water-soluble compounds in admixture can be used for optical brightening.

If desired, the amount of symmetrical water-insoluble compound in the reaction mixture can be reduced by carrying out the reaction in such a manner that altogether about 2 molar equivalents of monofunctional reaction components are used per molar equivalent of the bifunctional reaction component employed, in which case the molar ratio of component which contains sulpho groups to component which contains no sulpho groups can be between 1:1 and 10:1.

The compounds of the present invention defined hereinbefore have a more or less pronounced fluorescence when in solution or suspension. They can be used for optically brightening a very wide variety of synthetic man-made, regenerated man-made or natural organic materials or substances which contain such organic materials.

Without any restriction being implied by the following classification, examples of organic materials are:

I. Synthetic organic materials of high molecular weight
  (a) polymerisation products based on organic compounds containing at least one polymerisable carbon-carbon double bond, that is to say their homopolymers or copolymers as well as their aftertreatment products, for example, crosslinking, grafting or degradation products, polymer blends, or products obtained by modification of reactive groups, for example polymers based on $\alpha,\beta$-unsaturated carboxylic acids or derivatives of such carboxylic acids, especially on acrylic compounds, for example acrylic esters, acrylic acid, acrylonitrile, acrylic amides and their derivatives or their methacrylic analogs, and polymers based on vinyl and vinylidene compounds (for example vinyl alcohol);
  (b) polymerisation products which can be obtained by ring opening, for example, polyamides of the polycaprolactam type, and also polymers which are obtained both by polyaddition and by polycondensation, for example polyethers or polyacetals;
  (c) polycondensation products or precondensates based on bifunctional or polyfunctional compounds with condensable groups, their homocondensation and co-condensation products, and aftertreatment products, for example polyamides (for example hexamethylenediamine adipate), maleic resins, melamine resins, their precondensates and analogs, polycarbonates and silicones;
  (d) polyaddition products, such as polyurethanes (crosslinked and non-crosslinked) and epoxide resins.

II. Regenerated man-made organic materials, for example cellulose esters of varying degrees of esterification (acetate or triacetate) or cellulose ethers, regenerated cellulose (viscose or cuprammonium cellulose), or their aftertreatment products, and casein plastics. III. Natural organic materials of animal or vegetable origin, for example based on cellulose or proteins, such as cotton, wool, linen, silk, varnish gums, starch and casein.

The organic materials to be optically brightened can be in the most diverse states of processing (raw materials, semi-finished goods or finished goods). On the other hand, they can be in the form of structures of the most diverse shapes, for example predominantly three-dimensional sturctures such as sheets, profiles, injection mouldings, various machined articles, chips, granules or foams, and predominantly in the form of two-dimensional structures, such as films, foils, lacquers, coatings and impregnations, or of predominantly one-dimensional bodies, such as filaments, fibres, flocks and wires. The said materials can, on the other hand, also be in an unshaped state, in the most diverse homogeneous or inhomogeneous forms of distribution, for example, in the form of powders, solutions, emulsions, dispersions, latices, pastes or waxes.

Fibrous materials can be, for example, in the form of endless filaments (stretched or unstretched), staple fibres, flocks, hanks, textile filament yarns, threads, non-wovens, felts, waddings, flocked structures or woven textile or bonded textile fabrics, knitted fabrics and papers, cardboards or paper pulps.

The compounds to be used according to the invention are of importance, inter alia, for the treatment of organic textile materials, especially woven textile fabrics. If fibres which can be in the form of staple fibres or endless filaments or in the form of hanks, woven fabrics, knitted fabrics, fleeces, flocked substrates or bonded fabrics, are to be optically brightened according to the invention, this is advantageously effected in an aqueous medium, wherein the compounds in question are present in a finely disposed form (suspensions, or optionally solutions). If desired, dispersing agents, stabilisers, wetting agent and further assistants can be added during the treatment.

Depending on the type of whitener compound used, it can be advantageous to carry out the treatment in a neutral or alkaline or acid bath. The treatment is usually carried out at temperatures of 20° to 140° C., for example at the boiling point of the bath or near it (above 90° C.). Solutions or emulsions in organic solvents can also be used for finishing textile substrates according to the invention, as practised in the dyeing industry in so-called solvent dyeing (pad-heat fixing application, or exhaustion dyeing processes in dyeing machines).

The fluorescent whitening agents of the present invention can further be added to, or incorporated in, the materials before or during their shaping. Thus they can for example be added to the compression moulding composition or injection moulding composition during the manufacture of films, sheets, or mouldings.

The fluorescent whitening agents of the present invention can, for example, also be employed in the following use forms:
  (a) in mixtures with dyes (shading) or pigments (for example white pigments), or as an additive to dye baths, printing pastes, discharge pastes or reserve pastes, or for the aftertreatment of dyeings, prints or discharge prints;
  (b) in mixtures with carriers, wetting agents, plasticisers, swelling agents, antioxidants, ultraviolet absorbers, heat stabilisers and chemical bleaching agents (bleaching bath additives);
  (c) in admixture with crosslinking agents or finishing agents (for example starch or synthetic finishes), and in combination with a wide variety of textile finishing processes, especially synthetic resin finishes (for example creaseproof finishes, such as wash-and-wear, permanent-press or non-iron), as well as flameproof finishes, soft handle finishes, anti-static finishes, or antimicrobial finishes;
  (d) incorporation of the fluorescent whiteners in polymeric carriers (polymerisation, polycondensation or polyaddition products, in a dissolved or dispersed form, for use, for example, in coating agents, impregnating agents or binders (solutions, dispersions and emulsions) for textiles, non-wovens, papers and leather;
  (e) as additives to master batches;
  (f) as additives to a wide variety of industrial products in order to make them more easily marketable (for example improving the appearance of soaps, detergents, pigments);
  (g) in combination with other optically brightening substances.

If the brightening process is combined with textile treatment or finishing methods, the combined treatment can in many cases advantageously be carried out with the aid of appropriate stable preparations which contain the fluorescent whitener compounds in such a concentration that the desired white effect is achieved.

In certain cases, the fluorescent whiteners are made fully effective by an after-treatment. This can be, for example, a chemical treatment (for example acid treatment), a thermal treatment (for example heat) or a combined chemical/thermal treatment. Thus, for example, the appropriate procedure to follow in whitening a number of fibrous substrates, for example polyester fibres, with the fluorescent whitening agents of the present invention, is to impregnate these fibres with the aqueous dispersions or solutions of the whitener compounds at temperatures below 75° C., for example at room temperature, and to subject them to a dry heat treatment at temperatures above 100° C., it being generally advisable additionally to dry the fibrous material beforehand at moderately elevated temperature, for example at not less than 60° C. and up to about 130° C. The heat treatment in the dry state is then advantageously carried out at temperature between 120° and 200° C., for example by heating in a drying chamber, by ironing within the specified temperature range or by treatment with dry, superheated steam. The drying and dry heat treatment can also be carried out in immediate succession or combined in a single process step.

The amount of fluorescent whitening agent according to the invention to be used, referred to the weight of the material to be brightened, can vary within wide limits. A marked and lasting effect can be obtained even with very insignificant amounts, in certain cases 0.0001 percent by weight. But it is also possible to use amounts of up to approx. 0.8 percent by weight and more. For most practical purposes, it is preferable to use amounts between 0.0005 and 0.5 percent by weight.

The fluorescent whitening agents of this invention which contain sulpho groups are also particularly suitable for use as additives to wash liquors or heavy duty and domestic detergents, to which they can be added in various ways. They are appropriately added to wash liquors in the form of their solution in water or organic solvents or, in a finely divided form, as aqueous dispersions. They are advantageously added to domestic or heavy duty detergents in any stage of the manufacturing process of the detergents, for example to the slurry before the washing powder is atomised, or during the preparation of liquid detergent combinations. They can be added both in the form of a solution or dispersion in water or other solvents and, without assistants, as a dry powder. For example, the whitening agents can be mixed, kneaded or ground with the active detergents and, in this form, mixed with the finished washing powder. However, they can also be sprayed in a dissolved or pre-dispersed form on the finished detergent.

Suitable detergents are the known mixtures of active detergents, for example soaps in the form of chips and powders, synthetics (soluble salts of sulphonates of higher fatty alcohols), higher and/or polyalkyl-substituted arylsulphonic acids, sulphocarboxylic acid esters of medium to higher alcohols, fatty acid acylaminoalkyl- or acylaminoaryl-glycerol sulphonates and phosphoric acid esters of fatty alcohols. Suitable builders which can be used are, for example, alkali metal polyphosphates and polymetaphosphates, alkali metal pyrophosphates, alkali metal salts of carboxymethylcellulose and other soil redeposition inhibitors, alkali metal silicates, alkali metal carbonates, alkali metal borates, alkali metal perborates, nitrilotriacetic acid, ethylenediaminotetraacetic acid, foam stabilisers, such as alkanolamides of higher fatty acids. The detergents can further contain for example antistatic agents, fat restorative skin protection agents, such as lanolin, enzymes, anti-microbial agents, perfumes and colourants.

The new fluorescent whitening agents have the particular advantage that they are also active in the presence of active chlorine donors, for example, hypochlorite, and can be used without significant loss of effect in wash liquors containing non-ionic washing agents, for example alkylphenolpolyglycol ethers.

The compounds of the invention containing sulpho groups are added in amounts of 0.005 to 1% or more, based on the weight of the liquid or pulverulent finished detergent. Wash liquors which contain the indicated amounts of the claimed fluorescent whitening agents impart a brilliant appearance in daylight when used to wash textiles made from cellulose fibres, polyamide fibres, resin-finished cellulose fibres etc.

The washing treatment is carried out as follows, for example:

The textiles are treated for 1 to 30 minutes at 20° to 100° C. in a wash liquor which contains 1 to 10 g/kg of a built-up composite detergent and 0.05 to 1%, based on the weight of the detergent, of the claimed whitening agents. The liquor ratio can be 1:3 to 1:50. After they have been washed, the textiles are rinsed and dried in the usual manner. The wash liquor can contain 0.2 g/l of active chlorine (for example as hypochlorite) or 0.1 to 2 g/l of sodium perborate as a bleaching additive.

In the following examples, parts and percentages are always by weight, unless otherwise stated. Unless indicated to the contrary, melting points and boiling points are uncorrected.

EXAMPLE 1

15.1 g of sodium methylate (content: 92.8%) are charged in the course of 15 minutes at 40° to 45° C. into a well stirred solution of 19.9 g of 6-chloro-8-formyl-1,3-benzodioxane, 40.7 g of 4,4'-bis-(dimethylphosphonomethyl)-biphenyl (content: 98%) and 22.1 g of sodium benzaldehyde2-sulphonate (content: 94.4%) in 200 ml of anhydrous dimethyl formamide, while expelling the air with nitrogen. The resultant yellow suspension is stirred for a further 3 hours at 40° to 45° C., diluted with 200 ml of desalinated water, neutralised with formic acid, heated to the boil and filtered hot through a thoroughly preheated pressure filter. The residue is washed with 50 ml of a boiling mixture of 25 ml of dimethyl formamide and 25 ml of water. The filtrate is cooled and the crystallised product is collected by suction filtration, washed with 50 ml of a mixture of 25 ml of dimethyl formamide and 25 ml of water and dried in vacuo at 90° to 100° C. The product (19.3 g) is dissolved in 60 ml of boiling dimethyl formamide, and the solution is filtered clear with the addition of 2 g of activated charcoal, treated hot with 600 ml of ethanol, cooled, and the crystallised product is collected by suction filtration. The product is dissolved in 50 ml of boiling dimethyl formamide and 300 ml of ethanol are added to the solution. After cooling, the precipitate is collected by suction filtration, washed with 100 ml of ethanol, and dried in vacuo at 100° to 110° C. to yield 10.4 g of the product of the formula

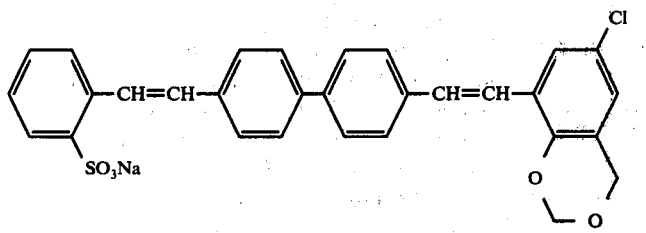

in the form of a yellow powder with blue fluorescence. Decomposition point: approx. 300° C. The residue of the first filtration is dried at 100° to 110° C. in vacuo. This product (13.6 g) is recrystallised twice from two 250 ml portions of toluene with fuller's earth and dried in vacuo at 100° to 110° C. to yield 10.1 g of the product of the formula

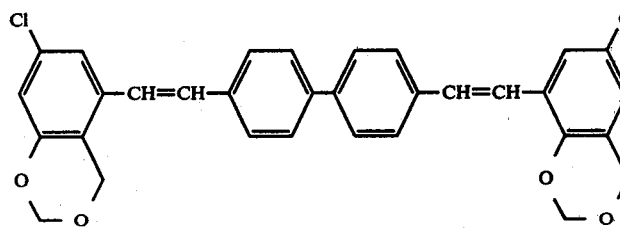

in the form of a yellow powder with yellowish green fluorescence.

Melting point: 239°–241° C.

The 4,4'-bis-(dimethylphosphonomethyl)-biphenyl of the formula

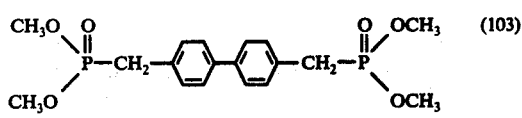

can be obtained by the process described in German Auslegeschrift No. 1,793,482.

Compounds (101) and (102) can also be obtained with equally good results by using the equivalent amount of 4,4'-bis-(diethylphosphonomethyl)-biphenyl instead of 4,4'-bis-(dimethylphosphonomethyl)-biphenyl. Potassium or sodium hydroxide powder can also be used as alkaline condensation agent instead of sodium methylate. Finally, dimethyl sulphoxide can also be used as solvent instead of dimethyl formamide.

The same procedure with the equivalent amount of tetraethyl p-xylylenediphosphonate instead of 4,4'-bis-(dimethylphosphonomethyl)-biphenyl yields the compounds of the formulae

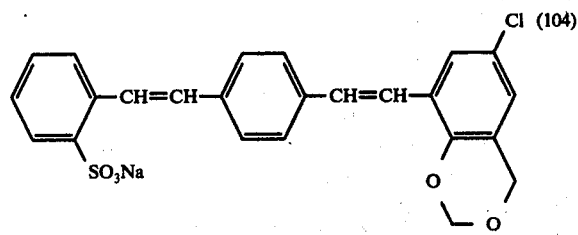

in the form of a yellow powder with greenish yellow fluorescence, and

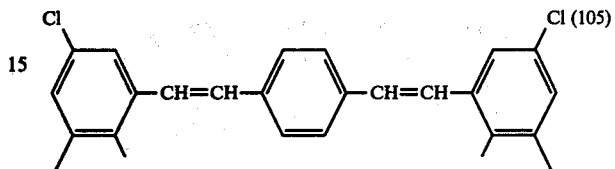
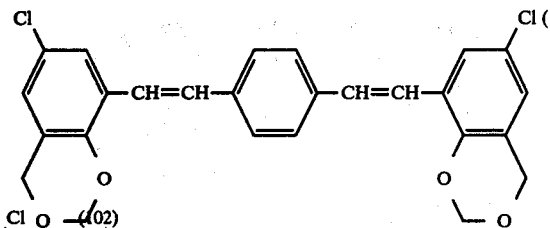

in the form of a yellow powder with yellowish green fluorescence.

Melting point: 234°–236° C.

EXAMPLE 2

Bleached cotton is washed in the liquor ratio 1:20 for 15 minutes in a warm liquor of 50° C. which contains, per liter, the following ingredients:

0.004 to 0.016 g of the compound of the formula (101),
0.25 g of active chlorine (Javelle water)
4 g of a washing powder of the following composition:
 15% of dodecylbenzenesulphonate
 10% of sodium lauryl sulphonate
 40% of sodium tripolyphosphate
 25.75% of anhydrous sodium sulphate
 7% of sodium metasilicate
 2% of carboxymethyl cellulose
 0.25% of ethylenediaminetetracetic acid.

The cotton is not put into the bath until 15 minutes after the warm wash liquor of 50° C. been prepared. After it has been rinsed and dried, the fabric has a good white effect of good fastness to acid, light and chlorine.

A good white effect is also obtained by carrying out the wash in the same way at 25° C.

EXAMPLE 3

A polyamide fabric (Perlon-Helanca) is washed in a liquor ratio of 1:20 for 15 minutes in a warm liquor of 50° C. which contains, per liter, the following ingredients:

0.004 to 0.016 g of the compound of the formula (101)
0.25 g of active chlorine (Javelle water)
4 g of a washing powder of the following composition:
 15% of dodecylbenzenesulphonate
 10% of sodium lauryl sulphonate 40% of sodium tripolyphosphate
25.75% of anhydrous sodium sulphate
7% of sodium metasilicate
2% of carboxymethyl cellulose
0.25% of ethylenediaminetetracetic acid.

The polyamide fabric is not put into the bath until 15 minutes after the warm wash liquor of 50° C. has been prepared. After it has been rinsed and dried, the fabric has a good white effect of good lightfastness.

A good white effect is also obtained by carrying out the wash in the same way at 25° C.

EXAMPLE 4

A polyamide fabric (Perlon) is put in the liquor ratio 1:40 at 60° C. into a bath which contains (referred to the weight of the fabric) 0.1% of the compound of the formula (101) and, per liter, 1 g of 80% acetic acid and 0.25 g of an adduct of 30 to 35 moles of ethylene oxide and 1 mole of industrial stearyl alcohol. The bath is heated in the course of 30 minutes to boiling temperature and kept at the boil for 30 minutes. After the fabric has been rinsed and dried, a good white effect is obtained.

Similar white effects are obtained by using a polyamide 66 (nylon) fabric instead of a polyamide 6 fabric Finally, the process can also be carried out under high temperature conditions, for example for 30 minutes at 130° C. For this type of application it is advisable to add 3 g/l of hydrosulphite to the bath.

EXAMPLE 5

A homogeneous mixture of 100 parts of polyvinyl chloride, 3 parts of a stabiliser (Advastat BD 100; Ba/Cd complex), 2 parts of titanium dioxide, 59 parts of dioctyl phthalate and 0.01 to 0.2 part of the compound of the formula (102) is rolled to a sheet on a calender at 150°–155° C. The resultant opaque polyvinyl chloride sheet has a substantially greater degree of whiteness than a sheet which does not contain the fluorescent whitener.

EXAMPLE 6

With exclusion of air, 100 parts of polystyrene and 0.1 part of the compound of the formula (102) are fused for 20 minutes at 210° C. in a tube of 1 cm diameter. After cooling, a whitened polystyrene mass of good lightfastness is obtained.

EXAMPLE 7

1.5 g of a matting agent, 1 g of titanium dioxide (rutil type) and 0.05 g of the compound of the formula (102) are stirred into a polyurethane coating compound consisting of 13.3 g of isocyanate-modified polyester, 26.7 g of ethyl acetate, 2 g of catalyst and 2 g of a polyfunctional isocyanate as crosslinking agent. This mixture is allowed to stand for 2 hours and subsequently coated with a doctor blade or a film drawing rod on a cotton fabric (wet film thickness 1 mm). After it has been dried at room temperature for 24 hours, the coated fabric has a strong white effect.

EXAMPLE 8

A polyester fabric (for example Dacron) is padded at room temperature with an aqueous dispersion which contains, per liter, 1 to 2 g of the compound of the formula (102) and 1 g of an adduct of approx. 8 moles of ethylene oxide and 1 mole of p-tert. octylphenol, and dried at approx. 100° C. The dried material is subsequently subjected to a heat treatment at 150° to 220° C. which, depending on the temperature, lasts from 2 minutes to a few seconds. The treated material has a good white effect.

I claim:

1. Distyryl compounds of the formula

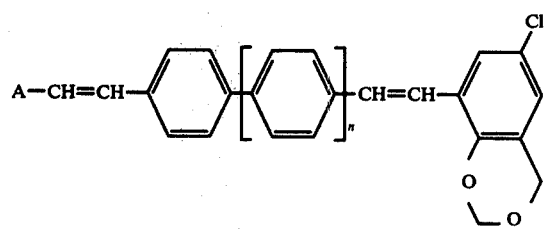

wherein A represents a radical of the formula

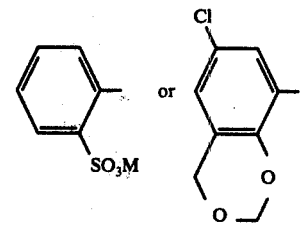

and $n$ is 0 or 1, whilst M represents a hydrogen atom or a salt-forming cation.

2. A distyryl compound according to claim 1 of the formula

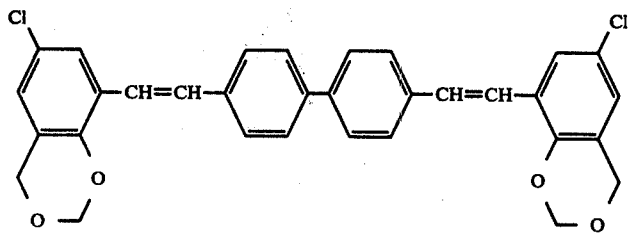

3. A distyryl compound according to claim 1 of the formula

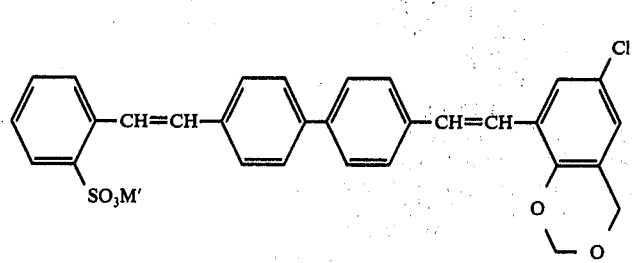

wherein M' represents an alkali metal, alkaline earth metal, ammonium or amine ion.

4. A distyryl compound according to claim 3 of the formula

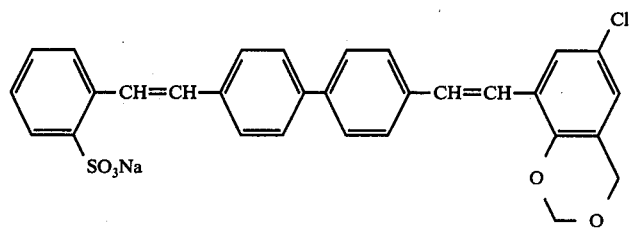

5. A distyryl compound according to claim 1 of the formula

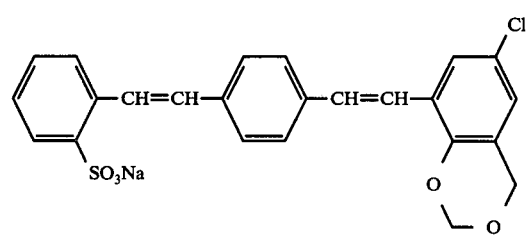

6. A distyryl compound according to claim 1 of the formula

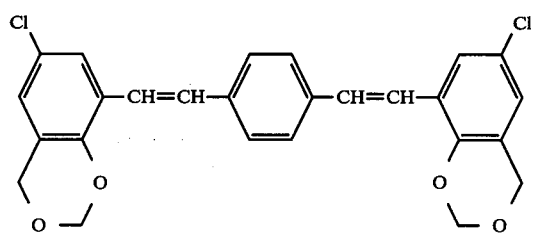

7. A process for optically brightening organic materials, which comprises incorporating in or applying to these materials an effective amount of a compound of the formula

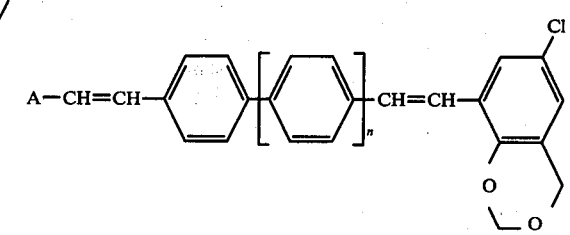

wherein A represents a radical of the formula

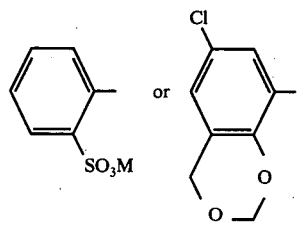

and $n$ is 0 or 1, whilst M represents a hydrogen atom or a salt-forming cation.

8. A process according to claim 7 for optically brightening polyvinyl chloride, polystyrene or polyurethanes, which comprises incorporating in or applying to these materials a compound of the formula

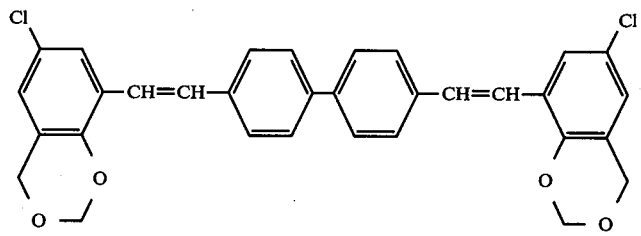

in an amount of 0.001 to 0.5 percent by weight, referred to the material to be brightened.

9. A process according to claim 7 for optically brightening materials made from cotton or polyamides which comprises incorporating in or applying to these materials an effective amount of a compound of the formula

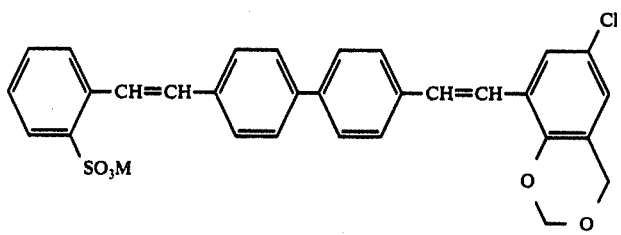
wherein M represents a hydrogen atom or a salt-forming cation.
10. A detergent which, in addition to conventional constituents of detergents, contains an effective optically brightening amount of a distyryl compound of the formula
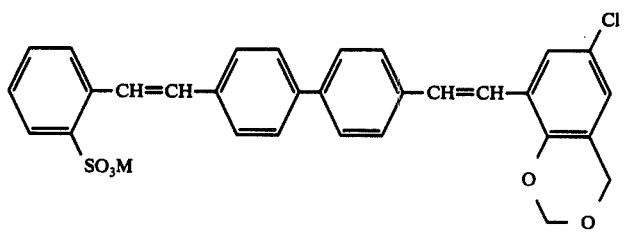
wherein M represents a hydrogen atom or a salt-forming cation.
* * * * *